United States Patent
Kugimoto et al.

(10) Patent No.: US 8,338,589 B2
(45) Date of Patent: Dec. 25, 2012

(54) PROCESS FOR PRODUCING LAUROLACTAM

(75) Inventors: Junichi Kugimoto, Ube (JP); Nobuhiro Ii, Ube (JP); Takashi Doi, Ube (JP); Satoru Fujitsu, Ube (JP); Tadashi Gotou, Ube (JP); Hideo Shimomura, Ube (JP); Ryouta Yasumatsu, Ube (JP); Joji Kawai, Ube (JP)

(73) Assignee: UBE Industries, Ltd., Ube-shi (JP)

( * ) Notice: Subject to any disclaimer, the term of this patent is extended or adjusted under 35 U.S.C. 154(b) by 139 days.

(21) Appl. No.: 12/993,451

(22) PCT Filed: May 19, 2009

(86) PCT No.: PCT/JP2009/059197
§ 371 (c)(1),
(2), (4) Date: Nov. 18, 2010

(87) PCT Pub. No.: WO2009/142206
PCT Pub. Date: Nov. 26, 2009

(65) Prior Publication Data
US 2011/0065913 A1    Mar. 17, 2011

(30) Foreign Application Priority Data

May 20, 2008 (JP) ............ 2008-131425
Oct. 20, 2008 (JP) ............ 2008-269262

(51) Int. Cl.
C07D 201/04    (2006.01)
C07D 225/02    (2006.01)
(52) U.S. Cl. ................................ 540/464
(58) Field of Classification Search ......... 540/464
See application file for complete search history.

(56) References Cited

U.S. PATENT DOCUMENTS

| | | | |
|---|---|---|---|
| 3,431,255 | A | 3/1969 | Strauss et al. |
| 2009/0093628 | A1 | 4/2009 | Ishii et al. |
| 2009/0306367 | A1 | 12/2009 | Roos et al. |
| 2010/0029931 | A1 | 2/2010 | Shibamoto et al. |

FOREIGN PATENT DOCUMENTS

| | | |
|---|---|---|
| DE | 102006058190 | 10/2007 |
| JP | S52-003118 B | 8/1977 |
| JP | H05-004964 A | 1/1993 |
| JP | A-2001-342174 | 12/2001 |
| JP | A-2006-219470 | 8/2006 |
| JP | A-2007-284415 | 11/2007 |
| JP | A-2008-156277 | 7/2008 |
| WO | WO 2007/125002 A1 | 11/2007 |
| WO | WO 2008/096873 A1 | 8/2008 |
| WO | WO 2009/069522 A1 | 6/2009 |

OTHER PUBLICATIONS

International Search report issued in corresponding PCT Application No. PCT/JP2009/059197 mailed Aug. 4, 2009.
International Preliminary Report on Patentability and Written Opinion corresponding to PCT Application No. PCT/JP2009/059197, issued Jan. 11, 2011.
Extended European Search Report issued in European Patent Application No. 09750568.9 on Mar. 2, 2012.
Furuya et al., "Cyanuric Chloride as a Mild and Active Beckmann Rearrangement Catalyst," J. Am. Chem. Soc., vol. 127, pp. 11240-11241, 2005.
Russell, R., "One-Pot Synthesis Aids Scale-Up and Data Collection", Pharmaceutical Technology, pp. 17 and 22, Nov. 2003.
Ishihara et al., Journal of American Chemical Society pp. 11240-11241 (2005).
International Search report issued in corresponding PCT Application No. PCT/JP2008/071044 mailed Feb. 24, 2009.
International Preliminary Report on Patentability and Written Opinion corresponding to PCT Application No. PCT/JP2009/059197, issued Jun. 8, 2010.

*Primary Examiner* — Bruck Kifle
(74) *Attorney, Agent, or Firm* — Knobbe Martens Olson & Bear LLP

(57) ABSTRACT

The present invention relates to a process for producing laurolactam from cyclododecanone oxime by liquid-phase rearrangement reaction using trichlorotriazine as a rearrangement catalyst. The present invention can provide a process which can solve the problem of termination of the reaction at a certain conversion, can prevent an inactive precipitate generated from trichlorotriazine from precipitating in the course of the reaction process, and can remove an inactive precipitate, an active intermediate and a residual catalyst.

9 Claims, 1 Drawing Sheet

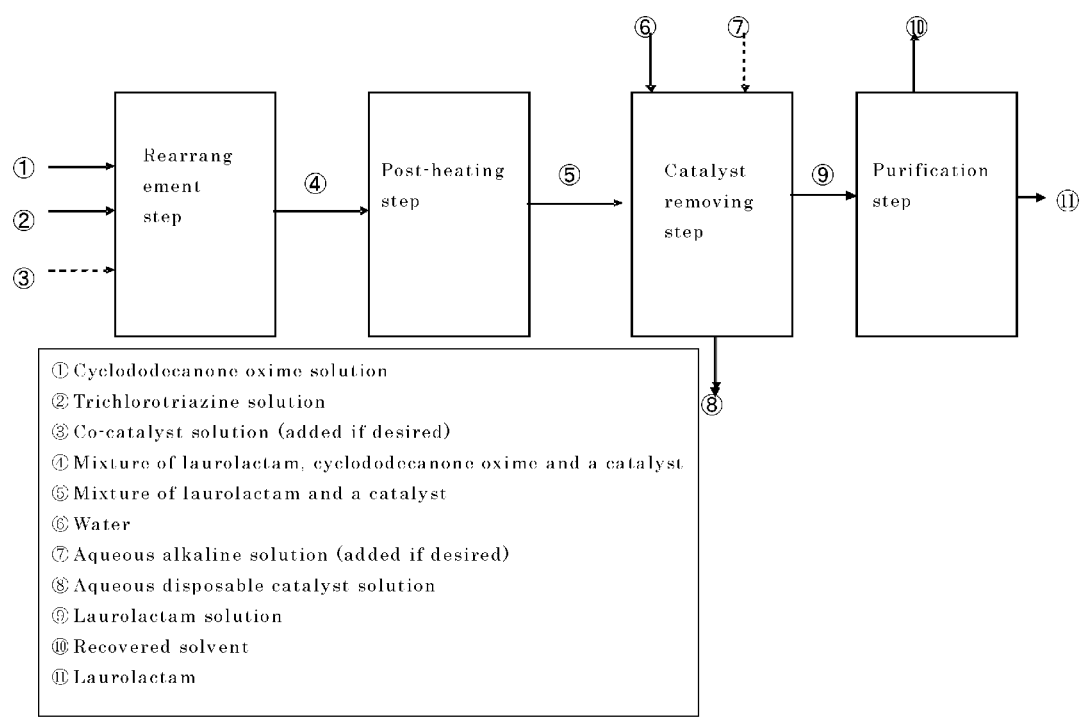

PROCESS FOR PRODUCING LAUROLACTAM

This application is the U.S. National Phase under 35 U.S.C. §371 of International Application PCT/JP2009/059197, filed May 19, 2009, designating the U.S., and published in Japanese as WO2009/142206 on Nov. 26, 2009, which claims priority to Japanese Patent Application No. 2008-131425, filed May 20, 2008; and to Japanese Patent Application No. 2008-269262, filed Oct. 20, 2008, the entire contents of which are incorporated herein by reference.

TECHNICAL FIELD

The present invention relates to an industrially useful process for producing laurolactam from cyclododecanone oxime.

BACKGROUND ART

A common industrial process for producing an amide compound involves Beckmann rearrangement of a corresponding oxime compound. For example, ε-caprolactam which is industrially useful is produced by Beckmann rearrangement of cyclohexanone oxime. Rearrangement catalysts used are generally concentrated sulfuric acid and oleum. Since these strong acids must be used in the stoichiometric amounts or more, they form a large amount of ammonium sulfate as a byproduct during neutralization. Although laurolactam, which is a starting material for Nylon 12, is also produced in a similar manner, the process is more complex because cyclododecanone oxime as an intermediate product has a high melting point. In producing ε-caprolactam, both cyclohexanone oxime and ε-caprolactam have relatively low melting points, so that oxime formation or rearrangement reaction can be conducted in a solvent-free system, but production of laurolactam requires a reaction solvent. This reaction solvent must be able to substantially dissolve cyclododecanone oxime and be inert to concentrated sulfuric acid or oleum, and therefore the selection of the solvent is considerably restricted.

The following references have described a known process for industrially producing laurolactam from cyclododecanone and an aqueous solution of hydroxylamine.

Patent Reference 1 has described the following process. Cyclododecanone is converted into an oxime using isopropylcyclohexane as a solvent, and after separating layers, a resulting solution of cyclododecanone oxime in isopropylcyclohexane is slowly added to concentrated sulfuric acid at a low temperature to prepare a solution of a cyclododecanone oxime sulfate adduct in sulfuric acid. After separating and recovering isopropylcyclohexane, the residual solution of cyclododecanone oxime sulfate adduct in sulfuric acid is heated to carry out Beckmann rearrangement of the oxime. After the rearrangement reaction, water is added to the system to dilute sulfuric acid and from the mixture, the laurolactam produced is extracted with an organic solvent. Here, the extraction solvent may be isopropylcyclohexane or cyclododecanone. The extraction solvent is recovered by distillation from the resulting extraction solution and then laurolactam in the residue is purified by distillation.

This process does not generate ammonium sulfate as a byproduct in the rearrangement reaction step, but requires enormously large facilities and energy for treating a large amount of waste diluted sulfuric acid. Furthermore, since cyclododecanone reacts with concentrated sulfuric acid to form a byproduct, the oxime-forming reaction must be completed for eliminating residual cyclododecanone, but due to hydrophobicity of isopropylcyclohexane, a mass transfer rate is low in an oil-water interface, leading to a longer oxime-forming reaction. As a whole, the process involves many steps of separation, recovery and recycling of solvents and, therefore, requires considerably large equipment expenses and energy.

Patent Reference 2 has described the following process. A mixture of cyclododecanone and cyclohexanone is blended with an aqueous solution of hydroxylamine to produce oximes. Cyclohexanone oxime produced has a low melting point and is a good solvent for cyclododecanone oxime, so that the reaction can be conducted at 100° C. or lower and at an ambient pressure. Furthermore, cyclohexanone oxime is adequately hydrophilic for the oxime-forming reaction to quickly proceed, and the mixture is transferred to the rearrangement step without residual cyclohexanone or cyclododecanone. A rearrangement catalyst used is concentrated sulfuric acid or oleum. Whereas laurolactam produced has a high melting point, it is highly soluble in caprolactam having a low melting point which is simultaneously produced. Therefore the reaction can be carried out even at a temperature of 100° C. or lower. The resulting rearrangement reaction solution is neutralized with ammonia water and then extracted with an organic solvent. Caprolactam can be dissolved in water to some extent, but is extracted into an organic solvent due to salting-out effect of ammonium sulfate formed by neutralization. Next, a large amount of water is added to the solution containing extracted laurolactam and caprolactam, and caprolactam is extracted into the aqueous phase. From the separated organic phase, the organic solvent is recovered and laurolactam is purified by distillation. On the other hand, the aqueous phase is concentrated and after removing impurities, caprolactam is purified.

This process is excellent in that laurolactam and caprolactam can be produced together. However, as a process for producing laurolactam, it has the following problems; (1) separation and purification of caprolactam requires large amounts of equipment expenses, resulting in low investment efficiency and the process involves operations of low energy efficiency such as concentration of an aqueous solution of caprolactam; (2) there is a restriction to a production ratio of laurolactam/caprolactam; and (3) caprolactam is a low-value-added product in comparison with laurolactam and an use efficiency of hydroxylamine is low.

Patent Reference 3 has described Beckmann rearrangement of an oxime compound in a polar solvent, wherein a rearrangement catalyst used is an aromatic compound (1) containing, as an aromatic-ring member, at least one carbon atom having a leaving group, (2) containing at least three aromatic-ring members, which are either or both of heteroatoms or/and carbon atoms having an electron-withdrawing group, and (3) wherein two of the heteroatoms and/or carbon atoms having an electron-withdrawing group are at the ortho- or para-position to the carbon atom having an electron-withdrawing group. Non-Patent Reference 1 has described in detail a rearrangement reaction using the rearrangement catalyst disclosed in Patent Reference 3. Focusing attention on a low yield of rearrangement when a non-polar solvent is used in Non-Patent Reference 1, Patent Reference 4, 5 and 6 have improved the yield and thus extended the range of solvents which can be used, to non-polar solvents. Generally, a non-polar solvent is more thermally and chemically stable, has a lower boiling point and has a smaller evaporative latent heat than a polar solvent, and thus, can be easily recovered and recycled, while it little dissolves a polar organic material or an inorganic material.

We have selected trichlorotriazine among the catalysts disclosed in Patent Reference 3, and have investigated its reaction with cyclododecanone oxime.

Patent Reference 3 and Non-Patent Reference 1 have explained a mechanism of the catalytic action of trichlorotriazine ($R_3$—Cl wherein $R_3$ represents dichlorotriazinyl) in Beckmann rearrangement of a ketoxime ($R_1$—C(—$R_2$)=N—OH wherein $R_1$ and $R_2$ represent alkyl or these may together form cycloalkane) as follows.

First, hydrogen chloride is eliminated from trichlorotriazine and the ketoxime to form $R_1$—C(—$R_2$)=N—O—$R_3$ (ether). By the rearrangement reaction, this ether is converted into $R_1$—N=C(—$R_2$)—O—$R_3$, to which the ketoxime is then added, and via a Meisenheimer complex ($R_1$—N=C(—$R_2$)—O—$R_3^-$—O$^+$—(H)—N=C($R_2$)—$R_1$), an amide ($R_1$—NH—C(=O)—$R_2$) is formed by elimination while $R_1$—C(—$R_2$)=N—O—$R_3$ is regenerated.

In accordance with the above mechanism, trichlorotriazine is rapidly consumed in the initial stage of the reaction to form cyclododecylideneaminoxydichlorotriazine (corresponding to $R_1$—C(—$R_2$)=N—O—$R_3$; hereinafter, referred to as "MOCT") and the reaction proceeds through the above reaction cycle, and therefore, this reaction cycle must be completed only by adding a catalytic amount of trichlorotriazine at the beginning of the reaction. It has been, however, found that when the reaction of cyclododecanone oxime is conducted using a catalytic amount of trichlorotriazine, the reaction stops at a certain conversion.

It is known that trichlorotriazine is hydrolyzed by water to give trioxytriazine. Trioxytriazine is catalytically inactive to the rearrangement. Furthermore, trichlorotriazine has three eliminable chlorine atoms and it is unclear how many chlorines should be hydrolyzed for making it inactive as a rearrangement catalyst. It can be, therefore, supposed that the rearrangement reaction can be completed by adding a small amount of trichlorotriazine if water is completely removed in a solution of cyclododecanone oxime to be rearranged. However, cyclododecanone oxime, which has a hydrophilic oxime group, is hygroscopic and it is, therefore, very difficult to make the cyclododecanone oxime absolutely dried.

On the other hand, in accordance with the above reaction mechanism, formation of MOCT is competitive to hydrolysis of trichlorotriazine, and when a rate of MOCT formation is larger than a rate of trichlorotriazine hydrolysis, a solution of cyclododecanone oxime is not necessarily absolutely dried.

We have first sampled and analyzed a reaction solution with the lapse of time for elucidating the mechanism of termination of the rearrangement reaction. As a result, it has been found that as the rearrangement reaction of cyclododecanone oxime proceeds, there is regenerated trichlorotriazine, which is gradually converted into trioxytriazine.

In other words, it has been supposed that in the initial reaction stage where the starting cyclododecanone oxime exists in an adequate amount, the reaction proceeds according to the reaction cycle, but in the final stage of the reaction, a cyclododecanone oxime concentration is so reduced that Meisenheimer-complex formation becomes slower, resulting in that 2-azacyclotridecanoxydichlorotriazine (corresponding to $R_1$—N=C(—$R_2$)—O—$R_3$) reacts with hydrogen chloride generated during formation of MOCT from trichlorotriazine and cyclododecanone oxime to generate laurolactam and to regenerate trichlorotriazine which is further hydrolyzed to give trioxytriazine, leading to termination of the rearrangement reaction.

Furthermore, since trioxytriazine generated as a result of hydrolysis of trichlorotriazine and its precursor are very insoluble in a non-polar solvent, they are precipitated in the reaction vessel and finally attach the vessel wall. Disadvantageously, precipitation of solids in the reaction vessel reduces a thermal conductivity coefficient of the reaction vessel, which makes operation unstable in a commercial apparatus. There are no literatures disclosing means for avoiding precipitation of such a catalyst residue within a reaction vessel.

Herein, an inactive precipitate which is formed by the change of the chemical structure of trichlorotriazine as a rearrangement catalyst added in the rearrangement step and lost rearrangement activity and precipitated as a solid, is distinguished from a residual catalyst whose chemical structure is unchanged and is dissolved in the reaction solution. Furthermore, a material whose chemical structure is changed but still retains its catalyst activity is called an active intermediate. A catalyst is a general name including the above three categories.

CITATION LIST

Patent Literature

Patent reference 1: Japanese examined patent publication No. S52-033118 (1977-033118)
Patent Reference 2: Japanese Laid-open patent publication No. H05-4964 (1993-4964).
Patent Reference 3: Japanese Laid-open patent publication 2006-219470.
Patent Reference 4: DE-102006058190
Patent Reference 5: Japanese Laid-open patent publication 2007-284415.
Patent Reference 6: Japanese Laid-open patent publication 2008-156277.

Non-Patent Literature

Non-Patent Reference 1: K. Ishihara, et. al., Journal of American Chemical Society, pp. 11240-11241(2005).

SUMMARY OF INVENTION

Technical Problem

An objective of this invention is to provide a process for producing laurolactam from cyclododecanone oxime by liquid-phase rearrangement reaction using trichlorotriazine as a rearrangement catalyst, which can solve the problem of termination of the reaction at a limited conversion, and/or can prevent an inactive precipitate generated from trichlorotriazine from precipitating in the course of the reaction process, and can remove an inactive precipitate, an active intermediate and a residual catalyst.

Solution to Problem

We have investigated a rearrangement reaction of cyclododecanone oxime using trichlorotriazine as a catalyst and has achieved the following invention.

The present invention relates to the followings.

In accordance with a first aspect of the present invention for solving the above problems, there is provided a process for producing laurolactam by a liquid-phase rearrangement reaction of cyclododecanone oxime using trichlorotriazine as a rearrangement catalyst, wherein a solution of cyclododecanone oxime is dehydrated such that the solution contains water in two-molar equivalents or less of trichlorotriazine.

In accordance with a second aspect of the present invention, there is provided a process for producing laurolactam comprising (a) a rearrangement reaction step where cyclododecanone oxime is subjected to liquid-phase rearrangement in a non-polar solvent using trichlorotriazine as a rearrangement catalyst to an extent that a conversion is 80% or more and less than 99%, (b) a post-heating step where the rearrangement reaction is completed, and (c) a catalyst removing step where an inactive precipitate, an active intermediate and a residual catalyst are removed.

Advantageous Effects of Invention

In a process for producing laurolactam by a liquid-phase rearrangement reaction of cyclododecanone oxime using trichlorotriazine as a rearrangement catalyst according to the present invention, the first aspect allows for highly selective production of laurolactam in a higher yield without termination of the reaction at a conversion, and the second aspect allows for industrially reliably producing laurolactam by preventing deposition of an inactive precipitate generated from trichlorotriazine in the course of the reaction and removing the inactive precipitate, an active intermediate and a residual catalyst.

BRIEF DESCRIPTION OF DRAWINGS

FIG. 1 schematically illustrates Example 28.

DESCRIPTION OF EMBODIMENTS

The present invention relates to a process for producing laurolactam by a liquid-phase rearrangement reaction of cyclododecanone oxime using trichlorotriazine as a rearrangement catalyst.

Unless otherwise stated, the following description is commonly applied to the first and the second aspects.

Cyclododecanone oxime as a starting material can be produced in a common manner. For example, it can be produced by adding hydrogen peroxide solution and ammonia water to cyclododecanone and then conducting ammoxidation in the presence of a catalyst, or by reacting cyclododecane with nitrosyl chloride in the presence of hydrogen chloride utilizing optical energy to prepare cyclododecanone oxime (photonitrosation). Although there has been recently described a process for producing it from cyclododecane and a nitrite using N-hydroxyphthalimide as a catalyst, a most-established industrial production method is reacting cyclododecanone with hydroxylamine.

Since cyclododecanone oxime has a high melting point, both reactions of oxime formation and rearrangement must be conducted in a solvent. When oxime formation and the rearrangement use the same solvent, a solvent used in the oxime-forming reaction can be used in the rearrangement reaction as it is, but when different solvents are used, a solvent must be replaced.

Examples of a solvent for the rearrangement reaction in the first aspect include nitriles such as acetonitrile and benzonitrile; esters such as ethyl acetate and butyl acetate; carboxylic acids such as acetic acid and propionic acid; aromatic hydrocarbons such as benzene, toluene and xylene; alicyclic hydrocarbons such as cyclooctane, cyclododecane and isopropylcyclohexane; and hydrogenated fused aromatic compounds such as decalin and tetralin. Among these solvents, aromatic hydrocarbons such as benzene, toluene and xylene; alicyclic hydrocarbons such as cyclooctane, cyclododecane and isopropylcyclohexane; and hydrogenated fused aromatic compounds such as decalin and tetralin may be also used as a solvent for the oxime-forming reaction and is preferable in the sense that the necessity of solvent replacement is eliminated. Furthermore, non-polar solvents including aromatic hydrocarbons such as benzene, toluene and xylene are particularly preferable because they have higher dissolving power for cyclododecanone oxime so that a rearrangement apparatus can be compact and energy for recovery and recycle of a solvent can be saved.

Examples of solvents which are suitable for the rearrangement reaction in the second aspect include, as described for the first aspect, nitriles, carboxylic acids, aromatic hydrocarbons, alicyclic hydrocarbons and hydrogenated fused aromatic compounds. Among these solvents, non-polar solvents such as aromatic hydrocarbons, alicyclic hydrocarbons and hydrogenated condensed aromatic compounds are preferable because they can be also used as a solvent for the oxime-forming reaction and can eliminate the necessity for solvent replacement. Furthermore, because of being non-polar, these solvents can be easily separated from an aqueous phase during washing a catalyst with water. Furthermore, they are thermally stable and has a small evaporative latent heat, so that recovery and recycle of a solvent is easy. Especially, aromatic hydrocarbons such as benzene, toluene and xylene are particularly preferable because they have higher dissolving power for cyclododecanone oxime and thus a rearrangement apparatus can be compact.

Such a rearrangement solvent, even a commercially available solvent, generally contains 100 to 300 ppm of water due to absorption of water in the air. Production of cyclododecanone oxime from cyclododecanone and hydroxylamine which is the most common process proceeds a two-phase reaction involving oil/aqueous phases, that is, a solution of oil-soluble cyclododecanone in the above solvent and an aqueous solution of water-soluble hydroxylamine, and cyclododecanone oxime having a hydrophilic oxime group is easily hydrated. Thus, after separation of an aqueous phase, a solution of cyclododecanone oxime contains 4000 to 10000 ppm of water.

There are no particular restrictions to a method for removing water dissolved in a solution of cyclododecanone oxime, but the most common method is co-evaporation with a solvent. Alternatively, after completely evaporating a solvent for oxime formation, solidified cyclododecanone oxime can be dried by heating under vacuum and a dried rearrangement solvent can be added before initiating the rearrangement reaction. As long as the rearrangement reaction is not inhibited, other dehydrating methods may be employed, including addition of a dehydrating agent such as molecular sieves and the use of a dehydrating membrane.

In the first aspect, the amount of water in a solution of cyclododecanone oxime after dehydration is two molar equivalents or less, preferably equimolar or less to trichlorotriazine as a rearrangement catalyst. In the second aspect, the amount of water in a solution of cyclododecanone oxime after dehydration is preferably two molar equivalents or less, more preferably equimolar or less to trichlorotriazine. Excessive residual water causes formation of trioxytriazine via hydrolysis of trichlorotriazine. Furthermore, the rearrangement reaction may be unfavorably incomplete, leading to deterioration in productivity due to the residual cyclododecanone oxime in the rearrangement reaction solution and the necessity for a step of separating cyclododecanone oxime from laurolactam. Alternatively, when the suitable amount of residual water in the cyclododecanone oxime solution is expressed as a concentration, it is preferably 2000 ppm or less, more preferably 600 ppm or less in the first and the second aspects. Since the acceptable water content depends on its ratio to trichlorotriazine used, increase of the amount of trichlorotriazine can expand the acceptable range of water content, but an excessively higher water concentration in a cyclododecanone oxime solution requires the use of a large amount of trichlorotriazine, leading to increase in a catalyst cost. Furthermore, hydrolysis of cyclododecanone oxime proceeds. An excessively high water concentration, therefore, leads to a lower yield of laurolactam.

A higher concentration of cyclododecanone oxime can advantageously improve productivity, but the concentration is limited by a solubility of cyclododecanone. For example, when the reaction is conducted using toluene as a solvent under an ambient pressure (boiling point: 110° C.), the upper limit of a cyclododecanone oxime concentration is 60% by weight.

The amount of trichlorotriazine depends on the type of a solvent, a water content and a concentration of cyclododecanone oxime, and is 0.05 mol % or more and 5.0 mol % or less to cyclododecanone oxime. In particular, when toluene is used as a solvent, a concentration of cyclododecanone oxime is 50% by weight and a water concentration in a cyclododecanone oxime solution is 600 ppm, the amount of trichlorotriazine is 0.3 mol % or more and 2.0 mol % or less, preferably 0.4 mol % or more and 1.0 mol % or less to cyclododecanone oxime.

A too small amount of trichlorotriazine unfavorably causes reduction in a reaction rate. A too large amount of trichlorotriazine unfavorably causes not only increase in a cost but also increase in a cost for removing a catalyst during purification of laurolactam.

In addition, an acid such as hydrogen chloride can be added as a co-catalyst to improve a rearrangement reaction rate. In particular, a Lewis acid is preferable because it can improve a rearrangement reaction rate without accelerating hydrolysis of cyclododecanone oxime. Examples of a Lewis acid include, but not limited to, zinc chloride, aluminum chloride, antimony pentachloride and tin tetrachloride, preferably zinc chloride and tin tetrachloride, particularly preferably zinc chloride which is significantly effective in improving a reaction rate. The amount of a Lewis acid is 0.1 mol % or more and 10 mol % or less, preferably 0.2 mol % or more and 5 mol % or less to cyclododecanone oxime. A too small amount of a Lewis acid is unfavorable because improvement in a rearrangement reaction rate cannot be observed. A too large amount of a Lewis acid is not favorable because a rearrangement reaction rate cannot be improved in proportion to the increase in the amount and a very large catalyst removing apparatus is required for removing the excessive Lewis acid and operations such us wastewater disposal is also troublesome.

A reaction temperature of the rearrangement reaction is 50° C. to 160° C., preferably 80° C. to 110° C. in the first aspect. In the second aspect, it is 50° C. to 160° C., preferably 70° C. to 110° C. A too low reaction temperature unfavorably reduces a reaction rate, leading to a longer reaction time. In addition, a too low reaction temperature unfavorably causes solubility of cyclododecanone oxime in a rearrangement solvent to be reduced, which causes the amount of the solvent used, recovered and recycled to be increased. A too high reaction temperature causes a temperature to be sharply increased due to heat generation in the rearrangement reaction, which is unfavorable in the light of controlling the reaction. A too high reaction temperature unfavorably causes side reactions such as a condensation reaction, which causes not only reduction in a yield of the rearrangement reaction but also deterioration in product quality such as stain.

A reaction time of the rearrangement reaction is generally 5 min to 10 hours, preferably 20 min to 4 hours. A reaction time depends on a catalyst concentration and a reaction temperature, and is adjusted under the above reaction conditions such that the reaction can be easily controlled and an excessively large reaction vessel is not required.

The reaction can be conducted under a reduced pressure, an ambient pressure or an increased pressure.

A closed process can be preferably employed because it can reduce a facility for adsorbing and detoxifying hydrogen chloride eliminated from trichlorotriazine and hydrogen chloride itself promotes the rearrangement reaction as a co-catalyst.

A rearrangement reaction apparatus can be selected from commonly used reaction apparatuses such as a batch type reaction apparatus, a tubular continuous reaction apparatus and an agitation vessel type continuous reaction apparatus, and an agitation vessel type continuous reaction apparatus is particularly suitable in the light of productivity and operational facility such as temperature control.

In the second aspect, we have found that increase in a conversion of cyclododecanone oxime facilitates formation of trioxytriazine. When a non-polar solvent is used as a rearrangement solvent, trioxytriazine, which is less soluble in the non-polar solvent, settles out as an inactive precipitate, which tends to adhere to the wall of the reaction vessel. Adhesion of the precipitate to the vessel wall reduces a heat conductivity of the wall, and makes it difficult to remove large amounts of heat generated from the rearrangement reaction by heat exchange, which leads to unstable operation in a commercial facility. It is, therefore, necessary to prevent trioxytriazine from precipitating during the rearrangement reaction, and to that end, the upper limit of a cyclododecanone oxime conversion is less than 99%, preferably less than 98%. In the second aspect, the reaction solution removed from the rearrangement reaction step is aged under heating in the subsequent post-heating step to complete the rearrangement reaction, and a reaction apparatus for the rearrangement reaction is preferably different from that for the post-heating step. A too low conversion of cyclododecanone oxime in the rearrangement step leads to large heat generation in the post-heating step, which requires active heat removal. There is, therefore, a lower limit for a conversion of cyclododecanone oxime in the rearrangement reaction step, which is 80% or more, more preferably 90% or more.

In the second aspect, both of the rearrangement reaction and the post-heating steps are steps for producing laurolactam by the rearrangement reaction of cyclododecanone oxime, and the former is aimed at selectively generating laurolactam by controlling a reaction rate through active heat removal while the latter is aimed at completing the rearrangement reaction of cyclododecanone oxime by retaining an rearrangement reaction solution only through heat retention or slight heating or cooling. Thus, precipitation of trioxytriazine or the like has a seriously adverse impact on the former, while giving little impact on the latter.

In the second aspect, a temperature in the post-heating step is 60° C. to 150° C., preferably 70° C. to 110° C. A too high heating temperature causes a laurolactam yield to be reduced due to side reactions such as condensation and lead to deterioration in laurolactam quality such as stain. A too low heating temperature causes laurolactam to settle out together with an inactive precipitate, requiring an apparatus for separating these. Furthermore, a larger post-heating apparatus is required for completing the rearrangement reaction. There are no particular restrictions to a retention time in the post-heating step as long as it ensures an adequate time for a conversion of cyclododecanone oxime to be preferably 99.8% or more. Even when a conversion of cyclododecanone oxime in the post-heating is low, high-quality laurolactam can be produced by purification through distillation, but a conversion is preferably 99.8% or more in the light of a cost for a distillation facility for removing/recovering cyclododecanone oxime and a utility cost.

In the second aspect, there are no particular restrictions to a post-heating apparatus, which can be any of reactor, vertical and tubular types, and a vessel type reaction apparatus is particularly suitable because it can easily discharge precipitated trioxytriazine. Agitation equipment, which is not essential, is effective for preventing an inactive precipitate from adhering to an apparatus wall, and a particularly preferable aspect involves mounting a scraper for scraping the settled inactive precipitate. Floating inactive precipitate may be drawn out from the top of the post-heating apparatus by overflow and then transferred to a catalyst removal step described later, but preferably, a settled inactive precipitate is removed from the apparatus bottom together with a solution of laurolactam and a part of them is recycled into the post-heating step while the remaining part is discharged to a catalyst removal step described later. Here, for example, a catalyst residue in the drawn solution can be removed by filtration for reducing a load in the catalyst removal step.

In the second aspect, the reactor bottom is preferably tapered toward an outlet for preventing a precipitate from depositing on the bottom. Heat generation in the post-heating step is smaller than that in the rearrangement step and thus the system temperature can be controlled by natural heat dissipation, but preferably, a simple heating/cooling apparatus such as a jacket is equipped.

In the second aspect, rearrangement reaction solution transferred to the catalyst removal step is washed with water under heating. By the water washing, all of the residual catalyst, the active intermediate and the inactive precipitate derived from trichlorotriazine as a rearrangement catalyst added in the rearrangement step is hydrolyzed into trioxytriazine, which is dissolved in water to be separated and removed. In the catalyst removal step, a temperature is 70° C. or higher, preferably 80° C. or higher, and the feeding amount of washing water is 35 times or more by weight, preferably 100 times or more by weight of the feeding amount of trichlorotriazine in the rearrangement step. A too low temperature or a too small amount of water may lead to remaining of the residual catalyst, the active intermediate and/or the inactive precipitate. A part of the residual catalyst, the active intermediate and the inactive precipitate have a cyclododecylidene-aminoxychlorotriazine structure derived from cyclododecanone oxime and trichlorotriazine, and if these remain without being hydrolyzed, a yield of laurolactam is unfavorably reduced. Contamination of laurolactam with an impurity having a triazine structure or a chlorine-containing compound unfavorably deteriorates quality of laurolactam. Furthermore, a chlorotriazine compound is pyrolytically decomposed to generate hydrogen chloride, which causes corrosion of an apparatus over time in the distillation step. Washing with water at a higher temperature or the use of a large amount of washing water is acceptable in the sense of removing a residual catalyst, but at a temperature of 95° C. or higher, a pressure device is required for preventing azeotropy of the process liquid. The use of washing water in 1000 times or more by weight merely increases wastewater. There are no particular restrictions to a processing apparatus as long as a unit for oil/water blending and an unit for separation between an oil and an aqueous phases; for example, an agitation mixing vessel and a reactor type separating vessel can be connected in use. An acid used as a co-catalyst is also water-soluble and thus can be removed by this step. An aqueous alkaline solution such as ammonia water and an aqueous sodium hydroxide solution can be, if desired, used for washing in order to remove a chlorine-containing impurity which may remain in a trace amount.

Laurolactam can be further purified by, typically, combining distillation (including separation as a distillate, drawing out as a bottom product and rectification) preferably in multiple steps. A solvent for the rearrangement reaction generally has a lower boiling point than laurolactam, so that a tank bottom (bottom product) after recovery of the solvent for the rearrangement reaction by distillation can be drawn out and can be purified by distillation one or more times.

There are no particular restrictions to the distillation conditions and a distillation apparatus in recovery and purification of a solvent, and distillation is desirably conducted under a reduced pressure at a vacuum degree of 10 torr or less such that a bottom temperature is 250° C. or less, preferably 220° C. or less for preventing ring-opening or polymerization of laurolactam.

EXAMPLES

There will be specifically described the present invention with reference to Examples. These examples merely illustrates embodiments of the present invention, but the present invention is not limited to the examples.

Reference Example 1

Production of Cyclododecanone Oxime

Into a pillow type first reactor for oxime formation with a 30 liter liquid phase zone which was internally divided into four chambers each of which was equipped with an agitating blade were fed a 15% by weight aqueous solution of hydroxylamine sulfate (Wako Pure Chemical Industries, Ltd.) at 1.5 kg/h and an oil phase from a second reactor for oxime formation. After adjusting a reaction temperature to 95° C., 25% by weight of ammonia water was fed into each chamber at 32 g/h to carry out the oxime-forming reaction. To the reaction solution was added toluene at 0.5 kg/h and the phases was separated to obtain an oil phase consisting of cyclododecanone oxime and toluene. The aqueous phase was fed to the second reactor for oxime formation. Into the second reactor for oxime formation, which was a pillow type reactor with a 15 liter volume which was internally divided into four chambers, were fed the aqueous phase of the above oxime-forming reaction solution and a 25% by weight solution of cyclododecanone in toluene at 2 kg/h (equimolar to hydroxylamine sulfate added to the first reactor), and after adjusting a reaction temperature to 95° C., a 25% by weight ammonia water was fed into each chamber at 16 g/h to carry out the oxime-forming reaction. The resulting reaction solution was separated and the oil phase was fed into the first reactor for oxime formation. To the aqueous phase was added toluene at 325 g/h, and cyclododecanone oxime dissolved in water was collected by countercurrent extraction and combined with the oil phase from the first reactor. A moisture content of the oil phase was determined by a Karl Fischer type moisture measuring instrument (Hiranuma AQ-2100 micro moisture measuring instrument) to be 4000 ppm by weight. Unless otherwise stated, ppm denotes ppm by weight and component ratio denotes molar ratio in the following Reference Examples, Examples and Comparative Examples.

Examples 1 to 27 and Comparative Examples 1 to 13 aimed at demonstrating relationship between a water content of a solution of cyclododecanone oxime used in the rearrangement reaction and a yield of laurolactam in the first aspect.

Examples 28 to 30 and Comparative Examples 14 to 17 aimed at not only demonstrating a relationship between a conversion of cyclododecanone oxime and a yield of laurolactam but also observing the presence of precipitate in the reaction step in the second aspect.

Relationship Between a Water Content of a Rearrangement Material and a Yield of Laurolactam Reference Example 2

Drying of Cyclododecanone Oxime

Cyclododecanone oxime used in Examples 1 to 27 and Comparative Example 1 to 13 was prepared as follows.

In 10 liter evaporator was placed 4 kg of the solution of cyclododecanone oxime in toluene obtained in Reference Example 1, and toluene was evaporated to obtain 790 g of cyclododecanone oxime. The resulting cyclododecanone oxime was placed in a vacuum dryer and dried at 120° C. under a reduced pressure of 150 Pa for 24 hours to give 740 g of dehydrated cyclododecanone oxime. A moisture content was determined in a dry box by a Karl Fischer type moisture measuring instrument to be 15 ppm.

Example 1

In 50 g of acetonitrile (Wako Pure Chemical Industries, Ltd.) were dissolved 10 g of dehydrated cyclododecanone oxime prepared in Reference Example 2, 0.467 g of trichlorotriazine (Wako Pure Chemical Industries, Ltd.) (cyclododecanone oxime concentration: 16.6% by weight; trichlorotriazine/cyclododecanone oxime (mol/mol): 0.05) to prepare a reactant solution. Moisture content measurement showed acetonitrile and the reactant material solution contained moisture in 450 ppm and 375 ppm, respectively. A water/trichlorotriazine ratio in the reactant material solution was 0.50. Here, preparation of the reactant solution and moisture measurement in the solvent were conducted in a dry box. The reactant solution in the closed vessel was removed from the dry box and heated with stirring under nitrogen atmosphere in an oil bath, and at 80° C. the reaction was conducted for 2 hours and was analyzed by gas chromatography (hereinafter, similar analysis was conducted in Examples and Comparative Examples), and as a result, a conversion of cyclododecanone oxime was 100% and a yield of laurolactam was 98.0%. Cyclododecanone probably generated by hydrolysis of cyclododecanone oxime was obtained in a yield of 0.7%. The reaction conditions and the results are shown in Table 1. The reaction results of Examples 2 to 26 and Comparative Examples 1 to 12 are also shown in Table 1.

Example 2

A reaction was conducted as described in Example 1 except that a reaction solvent was benzonitrile (Wako Pure Chemical Industries, Ltd.) containing water in 250 ppm and the amount of trichlorotriazine was reduced to 0.093 g.

Comparative Example 1

A reaction was conducted as described in Example 2 except that a reaction solvent was acetonitrile (water content: 450 ppm) used in Example 1 and a reaction time was increased to 4 hours.

Example 3

Calcined (300° C., 8 hours) molecular sieves 4A (Wako Pure Chemical Industries, Ltd.) was added to the acetonitrile used in Comparative Example 1, which was dried for 24 hours. A water content was reduced to 60 ppm. A reaction was conducted as described in Comparative Example 1, except that this dehydrated acetonitrile was used and a reaction time was 2 hours. A yield of cyclododecanone was reduced as shown in Table 1.

Example 4

A reaction was conducted as described in Example 1, except that a reaction solvent was toluene (water content: 310 ppm) and a reaction time was 3.5 hours.

Example 5

A reaction was conducted as described in Example 4, except that the amount of trichlorotriazine was reduced to 0.28 g.

Comparative Example 2

A reaction was conducted as described in Example 4, except that the amount of trichlorotriazine was reduced to 0.065 g and a reaction time was 6 hours.

Example 6

The reaction was conducted at 95° C. for 1 hour using, in addition to 10 g of cyclododecanone oxime and 0.093 g of trichlorotriazine, 0.069 g of zinc chloride as a co-catalyst and using 50 g of toluene dried as described for dehydrated acetonitrile in Example 3 (water content 40: ppm) as a solvent.

Example 7

A toluene having a water content of 336 ppm was prepared by adding water to the dehydrated toluene used in Example 6. A reaction was conducted as described in Example 6, except that this prepared toluene was used as a solvent.

Comparative Example 3

A toluene having a water content of 825 ppm was prepared by adding water to the dehydrated toluene used in Example 6. A reaction was conducted as described in Example 6, except that this prepared toluene was used as a solvent.

Example 8

A toluene having a water content of 1000 ppm was prepared by adding water to the dehydrated toluene used in Example 6. A reaction was conducted as described in Example 6, except that this prepared toluene was used as a solvent and trichlorotriazine and zinc chloride were increased to 0.262 g and 0.194 g, respectively.

Example 9

The reaction was conducted by adding 20 g of cyclododecanone oxime, 0.187 g of trichlorotriazine, 0.138 g of zinc chloride in 46.3 g of toluene dried as described for dehydrated acetonitrile in Example 3 (water content: 34 ppm).

Example 10

To the dehydrated toluene used in Example 9 was added water to prepare toluene having a water content of 390 ppm. A reaction was conducted as described in Example 9, except that this prepared toluene was used as a solvent.

Example 11

To the dehydrated toluene used in Example 9 was added water to prepare toluene having a water content of 770 ppm. A reaction was conducted as described in Example 9, except that this prepared toluene was used as a solvent.

Comparative Example 4

To the dehydrated toluene used in Example 9 was added water to prepare toluene having a water content of 1020 ppm. A reaction was conducted as described in Example 9, except that this prepared toluene was used as a solvent.

Comparative Example 5

To the dehydrated toluene used in Example 9 was added water to prepare toluene having a water content of 1910 ppm. A reaction was conducted as described in Example 9, except that this prepared toluene was used as a solvent.

Example 12

The reaction was conducted by adding 50 g of cyclododecanone oxime, 0.467 g of trichlorotriazine and 0.346 g of zinc chloride in 51 g of toluene dried as described in Example 3 (water content: 35 ppm).

Example 13

To the dehydrated toluene used in Example 12 was added water to prepare toluene having a water content of 1600 ppm. A reaction was conducted as described in Example 12, except that this prepared toluene was used as a solvent.

Comparative Example 6

To the dehydrated toluene used in Example 12 was added water to prepare toluene having a water content of 2500 ppm. A reaction was conducted as described in Example 12, except that this prepared toluene was used as a solvent.

Example 14

A reaction was conducted as described in Example 9, substituting methylcyclohexane dried over molecular sieves 4A (water concentration: 45 ppm) for the dehydrated toluene used in Example 9 as a solvent.

Example 15

To the dehydrated methylcyclohexane used in Example 14 was added water to prepare methylcyclohexane having a water content of 620 ppm. A reaction was conducted as described in Example 14, except that this prepared methylcyclohexane was used as a solvent.

Comparative Example 7

To the dehydrated methylcyclohexane used in Example 14 was added water to prepare methylcyclohexane having a water content of 890 ppm. A reaction was conducted as described in Example 14, except that this prepared methylcyclohexane (water concentration in the reactant solution: 622 ppm, water/trichlorotriazine: 2.27) was used as a solvent.

Example 16

A reaction was conducted as described in Example 9, substituting isopropylcyclohexane dried over molecular sieves 4A (water concentration: 55 ppm) for the dehydrated toluene used in Example 9 as a solvent.

Example 17

To the dehydrated isopropylcyclohexane used in Example 16 was added water to prepare isopropylcyclohexane having a water content of 700 ppm. A reaction was conducted as described in Example 16, except that this prepared isopropylcyclohexane was used as a solvent.

Comparative Example 8

To the dehydrated isopropylcyclohexane used in Example 16 was added water to prepare isopropylcyclohexane having a water content of 1100 ppm. A reaction was conducted as described in Example 16, except that this prepared isopropylcyclohexane was used as a solvent.

Example 18

A reaction was conducted as described in Example 9, substituting cyclooctane dried over molecular sieves 4A (water concentration: 35 ppm) for the dehydrated toluene used in Example 9 as a solvent.

Example 19

To the dehydrated cyclooctane used in Example 18 was added water to prepare cyclooctane having a water content of 770 ppm. A reaction was conducted as described in Example 18, except that this prepared cyclooctane was used as a solvent.

Comparative Example 9

To the dehydrated cyclooctane used in Example 18 was added water to prepare cyclooctane having a water content of 920 ppm. A reaction was conducted as described in Example 18, except that this prepared cyclooctane was used as a solvent.

Example 20

A reaction was conducted as described in Example 9, substituting decalin dried over molecular sieves 4A (water concentration: 30 ppm) for the dehydrated toluene used in Example 9 as a solvent.

Example 21

To the dehydrated decalin used in Example 20 was added water to prepare decalin having a water content of 685 ppm. A reaction was conducted as described in Example 20, except that this prepared decalin was used as a solvent.

Comparative Example 10

To the dehydrated decalin used in Example 20 was added water to prepare decalin having a water content of 1020 ppm.

A reaction was conducted as described in Example 20, except that this prepared decalin was used as a solvent.

Example 22

A reaction was conducted as described in Example 9, substituting cyclododecane dried by adding molecular sieves 4A to the molten material (water concentration: 55 ppm) for the dehydrated toluene used in Example 9.

Example 23

The dehydrated cyclododecane used in Example 22 was molten and water was added to prepare cyclododecane having a water content of 650 ppm. A reaction was conducted as described in Example 22, except that this prepared cyclododecane was used as a solvent.

Comparative Example 11

The dehydrated cyclododecane used in Example 22 was molten and water was added to prepare cyclododecane having a water content of 1050 ppm. A reaction was conducted as described in Example 22, except that this prepared cyclododecane was used as a solvent.

Example 24

Using cyclododecanone oxime (water concentration: 15 ppm) and the toluene (water concentration: 35 ppm) used in the Example 12, a reactant was prepared by adding 30 g of cyclododecanone oxime, 0.072 g of trichlorotriazine, 0.419 g of zinc chloride and 57.83 g of toluene, and a reaction was conducted at 100° C. for 1 hour.

Example 25

A reaction was conducted as described in Example 24, except that 0.034 g of trichlorotriazine and 35.25 g of toluene were used.

Comparative Example 12

To the toluene used in Example 24 was added water to prepare toluene having a water concentration of 440 ppm. A reactant was prepared by adding 30 g of cyclododecanone oxime, 0.102 g of trichlorotriazine, 0.635 g of zinc chloride and 45.88 g of the prepared toluene, and a reaction was conducted at 100° C. for 1 hour.

Example 26

A reaction was conducted as described in Comparative Example 12, except that the amount of trichlorotriazine was increased to 0.225 g.

The reaction results in Examples 1 to 26 and Comparative Examples 1 to 12 are shown in Table 1.

In the table, TCT, Ox12, Lc12 and CDON represent trichlorotriazine, cyclododecanone oxime, laurolactam and cyclododecanone, respectively (also applied to Table 2).

TABLE 1

| | Ox12 concentration wt % | TCT/Ox12 ratio mol % | ZnCl$_2$/Ox12 ratio mol % | Solvent | Water content in a reactant solution Weight ppm | H$_2$O/TCT (mol/mol) | Temperature °C. | Time h | Ox12 conversion (%) | Lc12 yield (%) | CDON yield (%) |
|---|---|---|---|---|---|---|---|---|---|---|---|
| Example 1 | 16.5 | 5.0 | 0.0 | Acetonitrile | 375 | 0.50 | 80 | 2.0 | 100.0 | 98.0 | 0.7 |
| Example 2 | 16.6 | 1.0 | 0.0 | Benzonitrile | 211 | 1.39 | 80 | 2.0 | 100.0 | 98.0 | 1.1 |
| Comparative Example 1 | 16.6 | 1.0 | 0.0 | Acetonitrile | 377 | 2.48 | 80 | 4.0 | 75.0 | 69.0 | 2.2 |
| Example 3 | 16.6 | 1.0 | 0.0 | Acetonitrile | 52 | 0.35 | 80 | 2.0 | 100.0 | 98.5 | 0.2 |
| Example 4 | 16.5 | 5.0 | 0.0 | Toluene | 259 | 0.34 | 80 | 3.5 | 100.0 | 96.2 | 1.1 |
| Example 5 | 16.6 | 3.0 | 0.0 | Toluene | 260 | 0.57 | 80 | 4.0 | 100.0 | 97.2 | 1.0 |
| Comparative Example 2 | 16.6 | 0.7 | 0.0 | Toluene | 261 | 2.45 | 80 | 6.0 | 45.0 | 41.8 | 1.7 |
| Example 6 | 16.6 | 1.0 | 1.0 | Toluene | 36 | 0.24 | 95 | 1.0 | 100.0 | 97.4 | 0.3 |
| Example 7 | 16.6 | 1.0 | 1.0 | Toluene | 282 | 1.86 | 95 | 1.0 | 100.0 | 96.4 | 0.3 |
| Comparative Example 3 | 16.6 | 1.0 | 1.0 | Toluene | 688 | 4.54 | 95 | 1.0 | 53.9 | 45.5 | 3.3 |
| Example 8 | 16.5 | 2.8 | 2.8 | Toluene | 830 | 1.96 | 95 | 1.0 | 99.6 | 96.1 | 1.5 |
| Example 9 | 30.0 | 1.0 | 1.0 | Toluene | 28 | 0.10 | 95 | 1.0 | 100.0 | 98.3 | 0.1 |
| Example 10 | 30.0 | 1.0 | 1.0 | Toluene | 276 | 1.01 | 95 | 1.0 | 100.0 | 98.1 | 0.4 |
| Example 11 | 30.0 | 1.0 | 1.0 | Toluene | 540 | 1.97 | 95 | 1.0 | 99.8 | 98.0 | 0.5 |
| Comparative Example 4 | 30.0 | 1.0 | 1.0 | Toluene | 713 | 2.60 | 95 | 1.0 | 89.4 | 85.1 | 0.7 |
| Comparative Example 5 | 30.0 | 1.0 | 1.0 | Toluene | 1332 | 4.86 | 95 | 1.0 | 22.4 | 21.3 | 2.2 |
| Example 12 | 49.1 | 1.0 | 1.0 | Toluene | 25 | 0.06 | 95 | 1.0 | 100.0 | 98.9 | 0.1 |
| Example 13 | 49.1 | 1.0 | 1.0 | Toluene | 809 | 1.81 | 95 | 1.0 | 99.6 | 97.8 | 0.6 |
| Comparative Example 6 | 49.1 | 1.0 | 1.0 | Toluene | 1260 | 2.81 | 95 | 1.0 | 87.0 | 80.9 | 1.6 |
| Example 14 | 30.0 | 1.0 | 1.0 | Methylcyclohexanone | 36 | 0.13 | 95 | 1.0 | 100.0 | 97.8 | 0.3 |
| Example 15 | 30.0 | 1.0 | 1.0 | Methylcyclohexanone | 435 | 1.59 | 95 | 1.0 | 99.8 | 97.6 | 0.4 |
| Comparative Example 7 | 30.0 | 1.0 | 1.0 | Methylcyclohexanone | 623 | 2.27 | 95 | 1.0 | 82.0 | 77.5 | 2.0 |
| Example 16 | 30.0 | 1.0 | 1.0 | Isopropylcyclohexane | 43 | 0.16 | 95 | 1.0 | 100.0 | 96.5 | 0.2 |
| Example 17 | 30.0 | 1.0 | 1.0 | Isopropylcyclohexane | 491 | 1.79 | 95 | 1.0 | 99.8 | 96.2 | 0.4 |
| Comparative Example 8 | 30.0 | 1.0 | 1.0 | Isopropylcyclohexane | 769 | 2.81 | 95 | 1.0 | 65.0 | 61.1 | 2.2 |
| Example 18 | 30.0 | 1.0 | 1.0 | Cyclooctane | 29 | 0.11 | 95 | 1.0 | 100.0 | 96.2 | 0.1 |
| Example 19 | 30.0 | 1.0 | 1.0 | Cyclooctane | 540 | 1.97 | 95 | 1.0 | 99.9 | 96.0 | 0.4 |
| Comparative Example 9 | 30.0 | 1.0 | 1.0 | Cyclooctane | 644 | 2.35 | 95 | 1.0 | 78.0 | 74.5 | 1.8 |
| Example 20 | 30.0 | 1.0 | 1.0 | Decalin | 25 | 0.09 | 95 | 1.0 | 100.0 | 97.3 | 0.1 |
| Example 21 | 30.0 | 1.0 | 1.0 | Decalin | 481 | 1.75 | 95 | 1.0 | 99.3 | 97.0 | 0.4 |
| Comparative Example 10 | 30.0 | 1.0 | 1.0 | Decalin | 713 | 2.60 | 95 | 1.0 | 78.0 | 72.9 | 1.9 |
| Example 22 | 30.0 | 1.0 | 1.0 | Cyclododecane | 43 | 0.16 | 95 | 1.0 | 100.0 | 96.1 | 0.2 |
| Example 23 | 30.0 | 1.0 | 1.0 | Cyclododecane | 456 | 1.66 | 95 | 1.0 | 99.8 | 96.0 | 0.4 |
| Comparative Example 11 | 30.0 | 1.0 | 1.0 | Cyclododecane | 734 | 2.68 | 95 | 1.0 | 75.0 | 68.3 | 2.0 |

TABLE 1-continued

|  | Ox12 concentration wt % | TCT/Ox12 ratio mol % | ZnCl₂/Ox12 ratio mol % | Solvent | Water content in a reactant solution | | Temperature °C. | Time h | Ox12 conversion (%) | Lc12 yield (%) | CDON yield (%) |
|---|---|---|---|---|---|---|---|---|---|---|---|
|  |  |  |  |  | Weight ppm | H₂O/TCT (mol/mol) |  |  |  |  |  |
| Example 24 | 34.0 | 0.3 | 2.0 | Toluene | 28 | 0.35 | 100 | 1.0 | 100.0 | 97.6 | 0.2 |
| Example 25 | 45.7 | 0.1 | 2.0 | Toluene | 26 | 0.51 | 100 | 1.0 | 99.8 | 96.6 | 0.1 |
| Comparative Example 12 | 39.1 | 0.4 | 3.1 | Toluene | 269 | 2.06 | 100 | 1.0 | 5.8 | 5.1 | 0.2 |
| Example 26 | 39.1 | 0.8 | 3.1 | Toluene | 269 | 0.94 | 100 | 1.0 | 98.2 | 96.0 | 0.4 |

Example 27

Water dissolved in the solution of cyclododecanone oxime in toluene prepared in Reference Example 1 was co-evaporated with toluene for dehydration. After the dehydration, the solution of cyclododecanone oxime in toluene has a water content of 135 ppm, and a concentration of cyclododecanone oxime was 46% by weight. This solution of cyclododecanone oxime was transferred to a rearrangement reactor consisting of three 1.5 liter vessel type reactors in series equipped with an agitation blade at a rate of 1.17 kg/h. To the first rearrangement reactor were fed a 5% by weight solution of trichlorotriazine in toluene at 0.1 kg/h and a 5% by weight solution of zinc chloride in toluene and laurolactam (weight ratio of toluene/laurolactam: 1/1) at 0.075 kg/h. The trichlorotriazine solution and the zinc chloride solution had a water content of 80 ppm and 800 ppm, respectively. Therefore, a ratio of water/trichlorotriazine fed into the rearrangement reactor was 0.46. The rearrangement reaction was conducted at a controlled temperature of 95° C., and at the outlet of the third reactor, cyclododecanone oxime was not detected as determined by gas chromatography, and a yield of laurolactam (corrected for the amount of laurolactam used for dissolving zinc chloride) was 96.6% and a yield of cyclododecanone was 0.3%.

Comparative Example 13

A rearrangement reaction was conducted as described in Example 27, except that the solution of cyclododecanone oxime in toluene was not dried. A ratio of water/trichlorotriazine fed to the rearrangement reactor was 9.70. Gas chromatographic analysis for the solution at the outlet of the reactor indicated that a conversion of cyclododecanone oxime, a yield of laurolactam and a yield of cyclododecanone were 42.0%, 35.7% and 0.3%, respectively. In each reactor, there was white precipitate, which was trioxytriazine (cyanuric acid) as determined by mass spectrometry.
Relationship Between a Conversion of Cyclododecanone Oxime and a Yield of Laurolactam Reference Example 3

Dehydration of a Solution of Cyclododecanone Oxime

Cyclododecanone oxime used for Examples 28 to 30 and Comparative Examples 14 to 17 was prepared as follows.
In 10 liter evaporator was placed the solution of cyclododecanone oxime in toluene obtained in Reference Example 1 (3.04 kg), which was subjected to co-evaporation of water with toluene and then concentrated to 1.80 kg. The solution of cyclododecanone oxime in toluene thus obtained was analyzed for a moisture content using a Karl Fischer type moisture measuring instrument, and a measured moisture content was 340 ppm. Assay for cyclododecanone oxime by gas chromatography (GL Sciences Inc., TC-1, using a 30 m capillary column) demonstrated that a cyclododecanone oxime concentration was 30.0% by weight. Although the cyclododecanone oxime solutions prepared as described in Reference Examples 1 and 3 were used in the following Examples and Comparative Examples, a water content varied a little and a catalyst and a co-catalyst solutions contained water, and therefore, for each run, a rearrangement reactor feeding solution was sampled and measured for a moisture content.

Example 28

Three 0.17 L glass agitation vessel type reaction apparatuses equipped with a propeller type agitator (a baffle and a heating/cooling jacket were mounted in the reactor) were connected in series, and to the first reactor were fed the solution of cyclododecanone oxime in toluene prepared in Reference Example 3 (hereinafter, referred to as Solution a) at 0.256 kg/h, a 5% by weight solution of trichlorotriazine in toluene (hereinafter, referred to as Solution b) at 0.016 kg/h, and a zinc chloride solution containing 5% by weight of zinc chloride, 47.5% by weight of laurolactam and 47.5% by weight of toluene (hereinafter, referred to as Solution c) at 0.011 kg/h, and the solutions were sequentially fed to the subsequent reactors in an overflow manner. In every reactor, a reaction temperature was 80° C. and an agitator rotation frequency was 500 rpm. A rearrangement reactor feeding solution had a water content of 472 ppm and a feed molar ratio of water/trichlorotriazine was 1.66. After the reaction became the steady state, the outlet solution of each reactor was sampled and analyzed by gas chromatography (using the column used in Reference Example 2), and cyclododecanone oxime conversion in reactors 1, 2 and 3 were 43.2%, 76.8% and 97.8%, respectively, and laurolactam yields were 42.8%, 76.4% and 96.8%, respectively. The reaction solution discharged from the third reactor was fed to a 0.17 L post-heating tank. In the post-heating tank, a Teflon® scraper was mounted on an anchor type agitation blade and the scraper was rotated at a low rate of 30 rpm to scrape an inactive precipitate while the reaction solution was discharged from the lower outlet, and after the precipitate was removed by filtration, the solution was recycled into the post-heating tank by pumping. Separately, an outlet by overflow was formed in the middle of the post-processing tank, and the discharged reaction solution was transferred to a 0.2 L catalyst-removing tank and washed with water at 0.03 L/h, and the oil and the aqueous phases were separated to obtain the oil phase, which is referred to as a crude laurolactam solution. The post-heating tank and the catalyst-removing tank were at 90° C. Gas chromatography of the crude laurolactam solution indicated that a conversion of cyclododecanone oxime was 99.9% and a yield of laurolactam was 99.4%. In the first to third reactor and the post-heating tank, adhesion or deposition of a precipitate was not observed. The filter was washed with hot water and the dissolved trioxytriazine was assayed by an automatic wavelength-selecting absorptiometer (Hach Company, model DR890) and was detected in 10.3 mol % to trichlorotriazine fed to the rearrangement section. Likewise, trioxytriazine in the washing water was assayed and detected in 88.5 mol % to trichlorotriazine fed to the rearrangement section. On the other hand, trioxytriazine or trichlorotriazine was not detected in the crude laurolactam solution by liquid chromatography.

Table 2 shows the experimental conditions in Examples and Comparative Examples and a cyclododecanone oxime conversion and a laurolactam yield for each reaction solution.

Example 29

A reaction was conducted as described in Example 28 under the conditions shown in Table 2. Adhesion or deposition of a precipitate was not observed in the each reactor or the post-heating tank. The amount of trioxytriazine trapped by a filter was 1.4 mol % to trichlorotriazine fed to the rearrangement section and the amount of trioxytriazine dissolved in the washing water was 97.5 mol % to trichlorotriazine fed to the rearrangement section, and trioxytriazine or trichlorotriazine was not detected in the crude laurolactam solution.

Comparative Example 14

A reaction was conducted as described in Example 29 under the conditions shown in Table 2. Adhesion or deposition of a precipitate was not observed in the first and the second rearrangement reactors, while in the third reactor, adhesion of a solid was observed on the reactor wall. The adhering material in the third reactor and a material trapped by the filter were dissolved in hot water and analyzed for trioxytriazine, and trioxytriazine was contained in 5.6% (the adhering material in the third reactor) and 4.8% (the filter-trapped material) to trichlorotriazine fed.

Comparative Example 15

A reaction was conducted as described in Comparative Example 14 under the conditions shown in Table 2. Only in the first reactor, adhesion of a precipitate was not observed, while in the second and the third reactors, solid adhesion was observed. The attached materials in the second and the third reactors and the trapped material by the filter were dissolved in hot water and assayed for trioxytriazine, and trioxytriazine was contained in 4.0% (the adhered material in the second reactor), 8.9% (the adhered material in the third reactor) and 1.0% (the filter-trapped material) to trichlorotriazine fed.

Comparative Example 16

The solution of cyclododecanone oxime in toluene prepared in Reference Example 1 was dried by adding dehydrated sodium sulfate, so that a water concentration was reduced to 1200 ppm. A reaction was conducted as described in Comparative Example 15 using this solution of cyclododecanone oxime in toluene. Precipitation of trioxytriazine was observed in the third reactor.

Example 30

Toluene was further evaporated from Solution a, to concentrate cyclododecanone oxime. To this solution was added zinc chloride, to prepare a toluene solution containing 49.8% by weight of cyclododecanone oxime and 0.34% by weight of zinc chloride (hereinafter, referred to as Solution d), which was then fed to a rearrangement reactor at 0.58 kg/h. At the same time, Solution b was fed to the rearrangement reactor at 0.039 kg/h. The reactors and the post-heating tank were set to 90, 90, 80 and 100° C., and the reaction was carried out. Temperatures of the heat media flowing in the jackets were 80, 81.5, 76.1 and 100.2° C., and the first to third reactors were kept at a predetermined temperature by cooling, while the post-heating tank did not have to be heated or cooled and was easily temperature-controlled. The results are shown in Table 2. Adhesion or deposition of a precipitate was not observed in the reactors or the post-heating tank. The amount of trioxytriazine trapped by the filter was 0.9 mol % to trichlorotriazine fed to the rearrangement section and the amount of trioxytriazine dissolved in the washing water was 98.0 mol % to trichlorotriazine fed to the rearrangement section, and trioxytriazine or trichlorotriazine was not detected in the crude laurolactam solution.

Comparative Example 17

A reaction was conducted as described in Example 30, except that the feeding amounts of Solutions d and b to the rearrangement reactor were 0.70 kg/h and 0.040 kg/h, respectively. Predetermined temperatures for the reactors and the post-heating tank were 90, 90, 80 and 100° C. while temperatures of the heat media flowing in the jackets were 82.7, 84.7, 77.4 and 95.1° C., so that the post-heating tank must be also cooled for heat removal.

The results are shown in Table 2. Adhesion or deposition of a precipitate was not observed in the reactors or the post-heating tank and the filter did not trap trioxytriazine, but the trioxytriazine dissolved in the washing water was as low as 80.1 mol % to trichlorotriazine fed to the rearrangement step.

TABLE 2

| | Feeding rate | | | | Temperature of reaction tank | | | | Water content | | Ox12 conversion | | | | Lc12 yield | | | |
|---|---|---|---|---|---|---|---|---|---|---|---|---|---|---|---|---|---|---|
| | | | | | Rearragement reactor | | | Post- | in a feeding solution | | | | | | | | | |
| | Solution a kg/h | Solution b kg/h | Solution c kg/h | Solution d kg/h | 1st reactor ° C. | 2nd reactor ° C. | 3rd reactor ° C. | heating tank ° C. | Water wt ppm | $H_2O$/TCT mol/mol | 1st reactor % | 2nd reactor % | 3rd reactor % | Crude Lc12 % | 1st reactor % | 2nd reactor % | 3rd reactor % | Crude Lc12 % |
| Example 28 | 0.256 | 0.016 | 0.011 | 0 | 80 | 80 | 80 | 90 | 472 | 1.66 | 43.2 | 76.8 | 97.8 | 99.9 | 42.8 | 76.4 | 96.8 | 99.4 |
| Example 29 | 0.486 | 0.027 | 0.018 | 0 | 90 | 90 | 80 | 90 | 513 | 1.98 | 45.0 | 79.1 | 92.8 | 99.8 | 44.9 | 78.3 | 91.9 | 98.7 |
| Comparative Example 14 | 0.428 | 0.023 | 0.017 | 0 | 90 | 90 | 90 | 90 | 391 | 1.55 | 59.5 | 90.6 | 99.5 | 99.9 | 58.3 | 88.4 | 97.8 | 97.9 |

TABLE 2-continued

| | Feeding rate | | | | Temperature of reaction tank | | | | Water content in a feeding solution | | Ox12 conversion | | | | Lc12 yield | | | |
|---|---|---|---|---|---|---|---|---|---|---|---|---|---|---|---|---|---|---|
| | | | | | Rearragement reactor | | | Post- | | | | | | | | | | |
| | Solution a kg/h | Solution b kg/h | Solution c kg/h | Solution d kg/h | 1st reactor °C. | 2nd reactor °C. | 3rd reactor °C. | heating tank °C. | Water wt ppm | H₂O/ TCT mol/ mol | 1st reactor % | 2nd reactor % | 3rd reactor % | Crude Lc12 % | 1st reactor % | 2nd reactor % | 3rd reactor % | Crude Lc12 % |
| Comparative Example 15 | 0.428 | 0.023 | 0.017 | 0 | 100 | 100 | 100 | 100 | 548 | 2.21 | 76.7 | 98.4 | 99.8 | 99.9 | 75.9 | 69.4 | 97.4 | 97.4 |
| Comparative Example 16 | 0.428 | 0.023 | 0.017 | 0 | 100 | 100 | 100 | 100 | 1215 | 4.90 | 62.3 | 82.0 | 86.8 | 90.3 | | | | |
| Example 30 | 0 | 0.039 | 0 | 0.58 | 90 | 90 | 80 | 100 | 187 | 0.62 | 46.1 | 77.9 | 90.4 | 99.9 | 45.4 | 77.4 | 89.4 | 98.9 |
| Comparative Example 17 | 0 | 0.040 | 0 | 0.70 | 90 | 90 | 80 | 100 | 187 | 0.62 | 41.6 | 64.1 | 73.6 | 96.1 | 39.5 | 60.2 | 71.3 | 92.0 |

Solution a: a 30.0% by weight solution of cyclododecanone oxime in toluene prepared in Reference Example 3.
Solution b: a 5% by weight solution of trichlorotriazine in toluene.
Solution c: a zinc chloride solution consisting of 5% by weight of zinc chloride, 47.5% by weight of laurolactam and 47.5% by weight of toluene.
Solution d: a toluene solution containing 49.8% by weight of cyclododecanone oxime and 0.34% by weight of zinc chloride.

What is claimed is:

1. A process for producing laurolactam by a liquid-phase rearrangement reaction of cyclododecanone oxime using trichlorotriazine as a rearrangement catalyst, wherein the rearrangement reaction is conducted under the conditions that a solution of cyclododecanone oxime contains water in two-molar equivalents or less of trichlorotriazine.

2. A process for producing laurolactam comprising:
 (a) subjecting cyclododecanone oxime to a liquid-phase rearrangement in a non-polar solvent using trichlorotriazine as a rearrangement catalyst, wherein a conversion is 80% or more and less than 99%;
 (b) completing the rearrangement reaction by post-heating; and
 (c) removing an inactive precipitate, an active intermediate and a residual catalyst
 wherein a reaction apparatus used in (a) is different from a reaction apparatus used in (b).

3. The process according to claim 2, wherein the cyclododecanone oxime solution used in the liquid-phase rearrangement contains water in two-molar equivalents or less of trichlorotriazine.

4. The process according to claim 1, wherein the cyclododecanone oxime solution used in the liquid-phase rearrangement contains water in 2000 ppm or less.

5. The process according to claim 1, wherein the cyclododecanone oxime solution used in the liquid-phase rearrangement contains water in 600 ppm or less.

6. The process according to claim 2, wherein a cyclododecanone oxime conversion in (b) is 99.8% or more.

7. The process according to claim 2, wherein said removing comprises washing with water.

8. The process according to claim 2, wherein the cyclododecanone oxime solution used in the liquid-phase rearrangement contains water in an amount of 2,000 ppm or less.

9. The process according to claim 2, wherein the cyclododecanone oxime solution used in the liquid-phase rearrangement contains water in an amount of 600 ppm or less.

* * * * *